(12) United States Patent
Nakashima et al.

(10) Patent No.: US 8,660,650 B2
(45) Date of Patent: Feb. 25, 2014

(54) ELECTROENCEPHALOGRAM ACTIVATION APPARATUS

(75) Inventors: Yusaku Nakashima, Tokyo (JP); Seiji Wada, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 13/468,366

(22) Filed: May 10, 2012

(65) Prior Publication Data

US 2012/0296390 A1 Nov. 22, 2012

(30) Foreign Application Priority Data

May 20, 2011 (JP) ................................. 2011-113452

(51) Int. Cl.
*A61N 1/00* (2006.01)
(52) U.S. Cl.
USPC .............................................. 607/45; 607/62
(58) Field of Classification Search
USPC ................................ 607/45, 62; 600/544, 545
See application file for complete search history.

(56) References Cited

U.S. PATENT DOCUMENTS 8,190,248 B2 * 5/2012 Besio et al. ................... 600/544

OTHER PUBLICATIONS

Lisa Marshall et al.; Boosting slow oscillations during sleep potentiates memory; Nature; vol. 444; pp. 610-613; Nov. 30, 2006.
Roumen Kirov et al.; Slow oscillation electrical brain stimulation during waking promotes EEG theta activity and memory encoding; PNAS; vol. 106, No. 36; Sep. 8, 2009.

* cited by examiner

*Primary Examiner* — Scott Getzow
(74) *Attorney, Agent, or Firm* — Dentons US LLP

(57) ABSTRACT

Provided is an electroencephalogram activation apparatus, including: an electroencephalogram acquisition unit configured to acquire brain waves of a user; an electrical stimulation unit configured to apply transcranial electrical stimulation to the scalp of the user; and a control unit configured to control the electrical stimulation unit based on the brain waves acquired by the electroencephalogram acquisition unit.

10 Claims, 6 Drawing Sheets

| Operation | Reference electrode | Comparison electrode | Change-over switch |
|---|---|---|---|
| Brain wave measurement | First electrode | Second electrode | OFF |
| Resistance measurement | First electrode | Second electrode | ON |
| TES | Third electrode | First electrode | ON |

ELECTROENCEPHALOGRAM ACTIVATION APPARATUS

BACKGROUND

The present technology relates to an electroencephalogram activation apparatus configured to activate brain waves with transcranial electrical stimulation.

An electroencephalogram (EEG) is a record of electrical activity that occurs in brains of living bodies (animals including humans), and there appear various waveforms such as an α wave, a slow wave, or a sleep spindle in accordance with a condition of brain activity. In other words, through measurement of brain waves, the condition of the brain activity can be judged.

In recent years, further studies have been conducted not only on the measurement of brain waves but also on "activation," that is, induction of brain waves through application of electrical stimulation to the head of a participant. Such electrical stimulation is referred to as transcranial electrical stimulation (TES). By inducing a desired brain wave through activation, brain activity can be promoted or suppressed. For example, the activation can be used for memory enhancement and treatment of psychiatric disorders.

For example, Non Patent Document 1 (Roumen Kirov, Carsten Weiss, Hartwig R. Siebner, Jan Born, and Lisa Marshall (2009), "Slow oscillation electrical brain stimulation during waking promotes EEG theta activity and memory encoding", Proc. Natl. Acad. Sci. USA, 106 (36) 15460-15465) describes that a θ wave (4 Hz to 8 Hz) can be amplified by applying transcranial slow oscillation stimulation (tSOS at a frequency of 0.75 Hz) to a brain during waking, to thereby enhance memory. Further, Non Patent Document 2 (Marshall L, Helgadottir H, Molle M, Born J (2006), "Boosting slow oscillations during sleep potentiates memory", Nature 444: 610-613.) describes that a sleep spindle can be amplified by transcranial application of oscillating potential at a frequency of 0.75 Hz to a brain during sleep, to thereby enhance long-term memory during sleep.

SUMMARY

However, in both the technologies described in the above-mentioned related art documents, an operator measures brain waves and applies transcranial electrical stimulation to the head of a participant in accordance with the brain waves thus measured. This is because, in order to effectively bring the transcranial electrical stimulation into action, it is necessary to apply the transcranial electrical stimulation with appropriate strength or at an appropriate timing in accordance with a condition of brain activity, which appears in the brain waves. Thus, it has been difficult to personally or domestically perform activation of brain waves.

In view of the above-mentioned circumstances, there is a need for an electroencephalogram activation apparatus capable of applying transcranial electrical stimulation in accordance with a condition of brain activity.

According to an embodiment of the present technology, there is provided an electroencephalogram activation apparatus including an electroencephalogram acquisition unit, an electrical stimulation unit, and a control unit.

The electroencephalogram acquisition unit is configured to acquire brain waves of a user.

The electrical stimulation unit is configured to apply transcranial electrical stimulation to the scalp of the user.

The control unit is configured to control the electrical stimulation unit based on the brain waves acquired by the electroencephalogram acquisition unit.

The brain waves acquired by the electroencephalogram acquisition unit include a brain wave activated by transcranial electrical stimulation applied by the electrical stimulation unit. Thus, in the electroencephalogram activation apparatus according to the embodiment of the present technology, the control unit controls the electrical stimulation unit based on the brain waves acquired by the electroencephalogram acquisition unit. With this, transcranial electrical stimulation can be applied in accordance with a condition of brain activity of the user.

The electrical stimulation unit may apply transcranial electrical stimulation at a certain frequency to the scalp of the user, and the control unit may control the electrical stimulation unit in accordance with potential density in a frequency range of a brain wave activated by the transcranial electrical stimulation at the certain frequency.

It has been found that a frequency of transcranial electrical stimulation and a frequency of a brain wave to be activated by the transcranial electrical stimulation are different from each other. Thus, potential density in a frequency range of a brain wave activated by transcranial electrical stimulation (brain wave power) directly reflects an influence of activation. Therefore, in the electroencephalogram activation apparatus according to the embodiment of the present technology, the control unit controls the electrical stimulation unit with reference to the potential density in the frequency range. With this, more effective transcranial electrical stimulation can be applied.

The control unit may judge one of a plurality of sleep stages of the user based on a characteristic waveform which appears in the brain waves, and control the electrical stimulation unit in accordance with the sleep stage.

The sleep stage indicates a depth of sleep of the user, and can be judged from the characteristic waveform of the brain waves. In this context, it has been known that, when transcranial electrical stimulation is applied to a sleeping user, effects of the transcranial electrical stimulation are different from each other in accordance with the sleep stage of the user. Thus, in the electroencephalogram activation apparatus according to the embodiment of the present technology, the control unit controls the electrical stimulation unit in accordance with the sleep stage of the user. With this, transcranial electrical stimulation can be applied at an effective timing.

The electroencephalogram acquisition unit may include
a first electrode to be held in contact with the scalp of the user,
a first amplifier having an input terminal to which the first electrode is connected, and
a second electrode connected to a ground potential and to be held in contact with the head of the user.

The electrical stimulation unit may include
a voltage source,
a resistor connected to the voltage source,
a second amplifier having
an inverting input terminal to which the resistor is connected, and
a non-inverting input terminal to which the ground potential is connected, and
a third electrode connected to an output terminal of the second amplifier and to be held in contact with the head of the user.

The control unit may be connected to an output terminal of the first amplifier and control the electrical stimulation unit based on a brain wave which is a potential difference between output of the first amplifier and the ground potential.

According to this configuration, an inverting amplifier circuit is formed in the electrical stimulation unit, and hence transcranial electrical stimulation in the electrical stimulation unit is prevented from having an influence on brain waves to be acquired by the electroencephalogram acquisition unit. Thus, the electroencephalogram activation apparatus according to the embodiment of the present technology is capable of acquiring brain waves and applying transcranial electrical stimulation simultaneously therewith.

The electroencephalogram acquisition unit may include
a first electrode to be held in contact with the scalp of the user,
an amplifier having an input terminal to which the first electrode is connected, and
a second electrode connected to a ground potential and to be held in contact with the head of the user.

The electrical stimulation unit may include
an electric current source,
a third electrode connected to the electric current source and to be held in contact with the scalp of the user, and
a fourth electrode connected to the electric current source and to be held in contact with the scalp of the user.

The control unit may be connected to an output terminal of the amplifier and control the electrical stimulation unit based on a brain wave which is a potential difference between output of the amplifier and the ground potential.

According to this configuration, there is a risk that the electroencephalogram acquisition unit detects not only brain waves but also transcranial electrical stimulation itself to be applied by the electrical stimulation unit. However, the control unit is capable of referring to potential density of the brain wave in the frequency range of being activated by transcranial electrical stimulation, and this potential density does not include potential density of the transcranial electrical stimulation itself. Thus, the control unit is capable of controlling the electrical stimulation unit based on the brain wave free from an influence of the transcranial electrical stimulation itself.

The electrical stimulation unit may apply slow oscillation as the transcranial electrical stimulation, and the control unit may control the electrical stimulation unit based on potential density of a brain wave within a frequency range of a θ wave.

It has been known that, when slow oscillation (0.75 Hz) is applied as transcranial electrical stimulation, a brain wave at a frequency of from 4 Hz to 8 Hz, that is, the θ wave is activated. Thus, in the electroencephalogram activation apparatus according to the embodiment of the present technology, when the electrical stimulation unit applies slow oscillation, the control unit uses potential density of a brain wave in the frequency range of the θ wave at the time of control.

With this, the transcranial electrical stimulation (slow oscillation) can be effectively applied.

The control unit may apply the transcranial electrical stimulation to the electrical stimulation unit when the sleep stage is Stage 2, and may be free from applying the transcranial electrical stimulation to the electrical stimulation unit when the sleep stage is other than Stage 2.

It has been known that, when the transcranial electrical stimulation is applied in a case where the sleep stage of the user is Stage 2, transition from short-term memory to long-term memory is promoted. Thus, in the electroencephalogram activation apparatus according to the embodiment of the present technology, the control unit applies transcranial electrical stimulation only when having judged that the sleep stage of the user is Stage 2. With this, transcranial electrical stimulation can be applied at an effective timing.

As described above, according to the embodiment of the present technology, it is possible to provide an electroencephalogram activation apparatus capable of applying transcranial electrical stimulation in accordance with a condition of brain activity.

These and other objects, features and advantages of the present disclosure will become more apparent in light of the following detailed description of best mode embodiments thereof, as illustrated in the accompanying drawings.

DETAILED DESCRIPTION OF EMBODIMENTS (First Embodiment)

Description is made of an electroencephalogram activation apparatus according to a first embodiment.

<Functional Configuration of Electroencephalogram Activation Apparatus>

Figure 1:
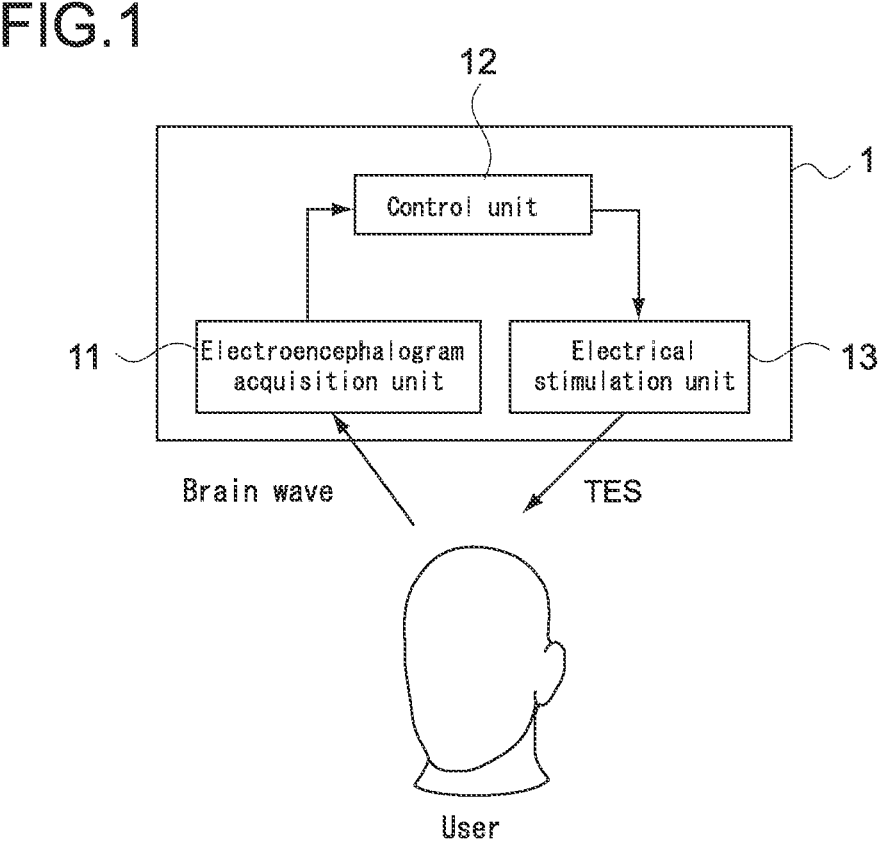
FIG. 1 is a block diagram showing a functional configuration of an electroencephalogram activation apparatus according to a first embodiment.

FIG. 1 is a block diagram showing a functional configuration of the electroencephalogram activation apparatus 1 according to the first embodiment;

As shown in FIG. 1, the electroencephalogram activation apparatus 1 includes an electroencephalogram acquisition unit 11, a control unit 12, and an electrical stimulation unit 13. The electroencephalogram acquisition unit 11 is connected to the control unit 12, and the control unit 12 is connected to the electrical stimulation unit 13.

The electroencephalogram acquisition unit 11 acquires brain waves of a user as potential waveforms with respect to time through intermediation of electrodes in contact with the scalp (surface of the head) of the user. The electroencephalogram acquisition unit 11 outputs the acquired brain waves to the control unit 12.

The control unit 12 controls the electrical stimulation unit 13 based on the brain waves fed from the electroencephalogram acquisition unit 11. Specifically, the control unit 12 is capable of performing a predetermined analysis process (described below) on the brain waves, to thereby control the electrical stimulation unit 13 based on the results of the analysis.

The electrical stimulation unit 13 applies transcranial electrical stimulation (TES) to the scalp of the user through intermediation of the electrodes in contact with the scalp of the user. TES is a weak electric current (several mA) conducted from the scalp of the user to the brain of the user through the cranium (cranial bone). TES includes transcranial direct current stimulation (tDCS) using a direct current and transcranial alternate current stimulation (tACS) using an alternating current. The electroencephalogram activation apparatus according to this embodiment is applicable to either tDCS or tACS.

TES applied from the electrical stimulation unit 13 to the scalp of the user is set to a predetermined frequency. This frequency is determined in accordance with a frequency of a brain wave desired to be activated (brain wave desired to be induced). For example, it has been proved that a brain wave at a frequency of from 4 Hz to 8 Hz, that is, a θ wave is activated by application of TES with slow oscillation (0.75 Hz). Similarly, when a relation between a frequency of TES and a frequency of a brain wave to be activated is found, the electrical stimulation unit 13 can be set such that TES with that frequency can be applied. Note that, with regard to the frequency of TES, TES can be performed with a frequency of alternating current pulses in a case of tACS, and can be performed with a frequency of direct current pulses in a case of tDCS.

The control unit 12 controls how the electrical stimulation unit 13 applies TES, for example, controls a current value and a stimulation timing of TES. The control unit 12 controls the electrical stimulation unit 13 based on the brain wave acquired by the electroencephalogram acquisition unit 11 as described above, and hence the electroencephalogram activation apparatus 1 is allowed to apply TES in accordance with a condition of brain activity of the user.

<How Control Unit Performs Control>

As described above, the control unit 12 is capable of performing the predetermined analysis process on the brain wave acquired by the electroencephalogram acquisition unit 11 and controlling the electrical stimulation unit 13 based on the results of the analysis.

Specifically, the control unit 12 is capable of calculating "potential density" of the brain wave and controlling the electrical stimulation unit 13 with use of the potential density.

Figure 2:
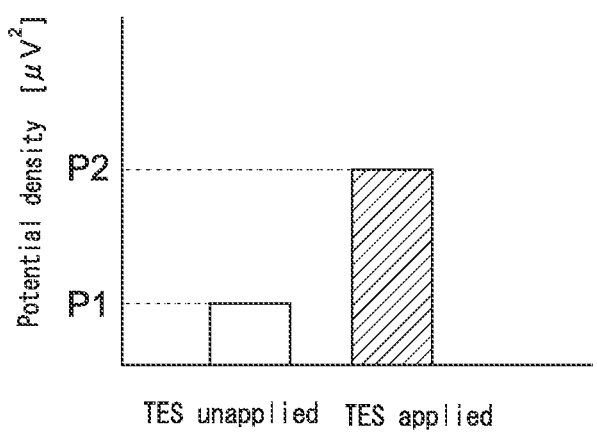
FIG. 2 is a graph showing examples of brain wave potential density.

The potential density, which can be obtained by performing a fast fourier transform on the brain wave, indicates power of a brain wave (brain wave power) within a predetermined frequency range. FIG. 2 is a graph showing examples of the brain wave potential density ($\mu V^2$) in a predetermined frequency range, which is calculated by the control unit 12. As shown in FIG. 2, when the brain wave potential density within a certain frequency range under a state in which TES is not applied is represented by P1, and when the brain wave potential density within the same frequency range under a state in which TES is applied is represented by P2, the difference P2−P1 corresponds to potential density of a brain wave activated by TES.

The control unit 12 is capable of calculating potential density of the brain wave within a frequency range in which the brain wave is activated by TES applied from the electrical stimulation unit 13 to the scalp of the user. For example, as in the above-mentioned example, when the electrical stimulation unit 13 applies TES at the frequency of 0.75 Hz, potential density of the brain wave at the frequency of from 4 Hz to 8 Hz can be calculated. This enables the control unit 12 to directly grasp an effect of activation by TES and provide feedback of the effect to the electrical stimulation unit 13.

Figure 3:
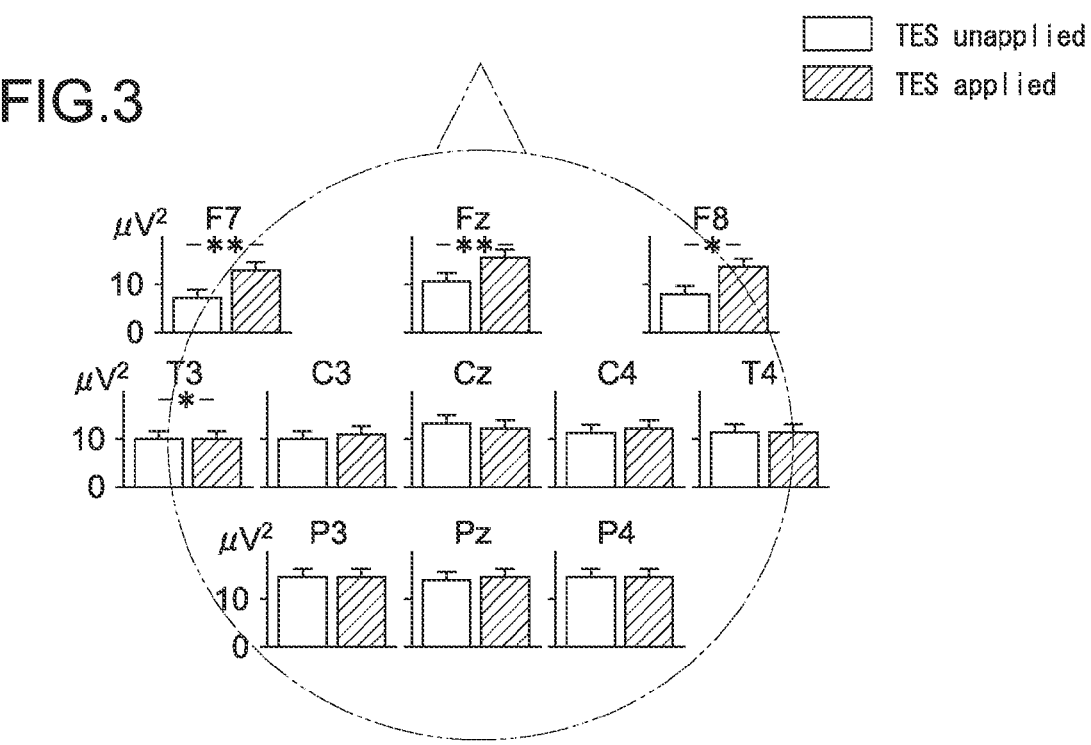
FIG. 3 is graphs showing an example of changes in brain wave potential density at positions on the scalp of a user.
Figure 4:
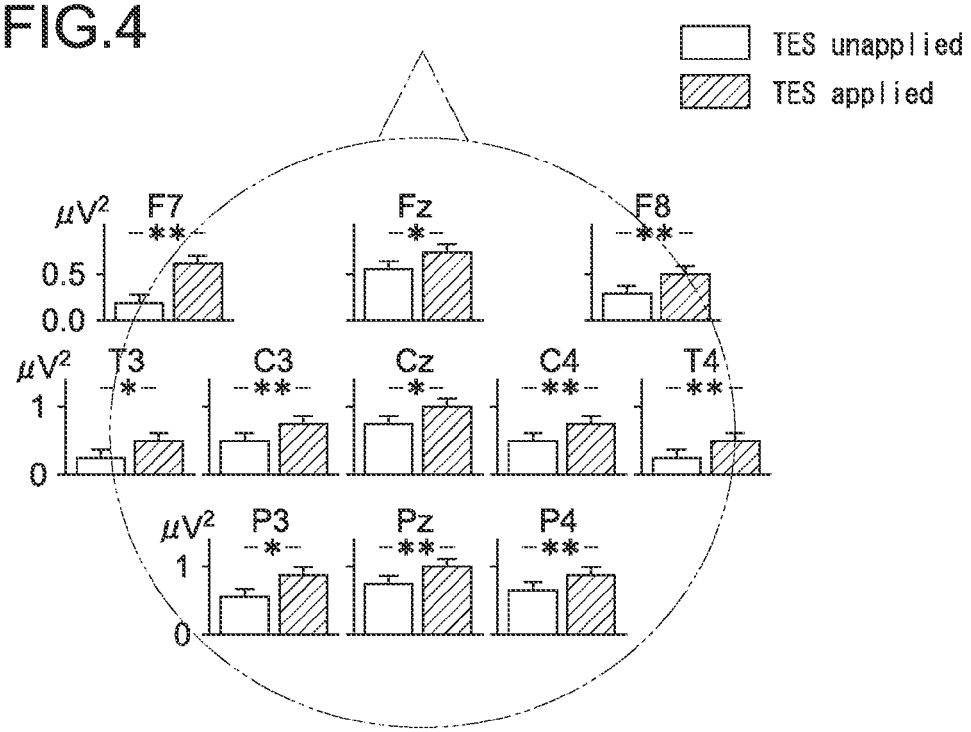
FIG. 4 is graphs showing another example of changes in brain wave potential density at positions on the scalp of the user.

FIGS. 3 and 4 are each graphs showing an example of changes in brain wave potential density at positions on the scalp of the user. FIGS. 3 and 4 each show potential density under a state in which TES is not applied (TES unapplied) and potential density under a state in which TES at the frequency of 0.75 Hz is applied (TES applied).

FIG. 3 shows potential density of the brain wave at the frequency of 0.75 Hz (slow oscillation), and FIG. 4 shows potential density of the brain wave at the frequency of from 4 Hz to 8 Hz (θ wave).

As shown in FIG. 3, when a frequency at which potential density is calculated is equal to that of TES, that is, equal to 0.75 Hz, difference between potential density in the case where TES is applied and potential density in the case where TES is not applied is small. This indicates that a component having the frequency of 0.75 Hz is small (or not contained) in the brain wave activated by TES at the frequency of 0.75 Hz. Further, the frequency at which potential density is calculated is equal to that of TES, that is, equal to 0.75 Hz, and hence there is a risk that TES itself is detected.

In contrast, as shown in FIG. 4, when a frequency range in which potential density is calculated ranges from 4 Hz to 8 Hz, differences can be found between potential density in the case where TES is applied and potential density in the case where TES is not applied. This indicates that the brain wave at the frequency of from 4 Hz to 8 Hz is activated by TES at the frequency of 0.75 Hz. Further, the frequency of 0.75 Hz which is the frequency of TES does not fall within the frequency range in which potential density is calculated, and hence this potential density does not include TES itself.

In other words, when the control unit 12 calculates potential density in the frequency range of the brain wave activated by TES, it can be judged that change in the potential density is caused by the activation. Thus, the control unit 12 is capable of setting a threshold value of potential density, thereby controlling the electrical stimulation unit 13; specifically, increasing TES when the calculated difference in potential density (P2−P1) is smaller than the threshold value, and reducing or stopping TES when the calculated difference is larger than the threshold value.

As described above, the electroencephalogram activation apparatus 1 is capable of applying more effective TES to the user with reference to the potential density in the frequency range of the brain wave activated by TES.

Further, the control unit 12 is also capable of judging a "sleep stage" based on brain waves so as to control the electrical stimulation unit 13 in accordance with the sleep stage. The sleep stage is an index of a degree of sleep of humans, which is generally used in the field of sleep. "REM Sleep," "Non-REM Sleep Stage 1," "Non-REM Sleep Stage 2," "Non-REM Sleep Stage 3," and "Non-REM Sleep Stage 4" are defined. The sleep stage can be judged based on brain waves, or when necessary, on an electrooculogram (EOG), an electromyogram (EMG), and the like.

By applying TES while the user is in a sleep state of Stage 2 described above, a "sleep spindle" can be activated. The sleep spindle is one of a waveform of brain waves, and it has been known that memory is more effectively enhanced (transition from short-term memory to long-term memory is promoted) in proportion to the number of sleep spindles. Thus, when the control unit 12 judges based on brain waves that the sleep stage is Stage 2 and causes the electrical stimulation unit 13 to apply TES, activation can be performed at an effective timing.

In addition, the control unit 12 is capable of controlling the electrical stimulation unit 13 such that TES is applied or not in a predetermined sleep stage for the purpose other than memory enhancement, such as stabilization of sleep. In this way, the electroencephalogram activation apparatus 1 is capable of adjusting a TES application timing in accordance with the sleep stage, and hence more effective TES can be applied to the user.

<Circuit Configuration of Electroencephalogram Activation Apparatus>

Figure 5:
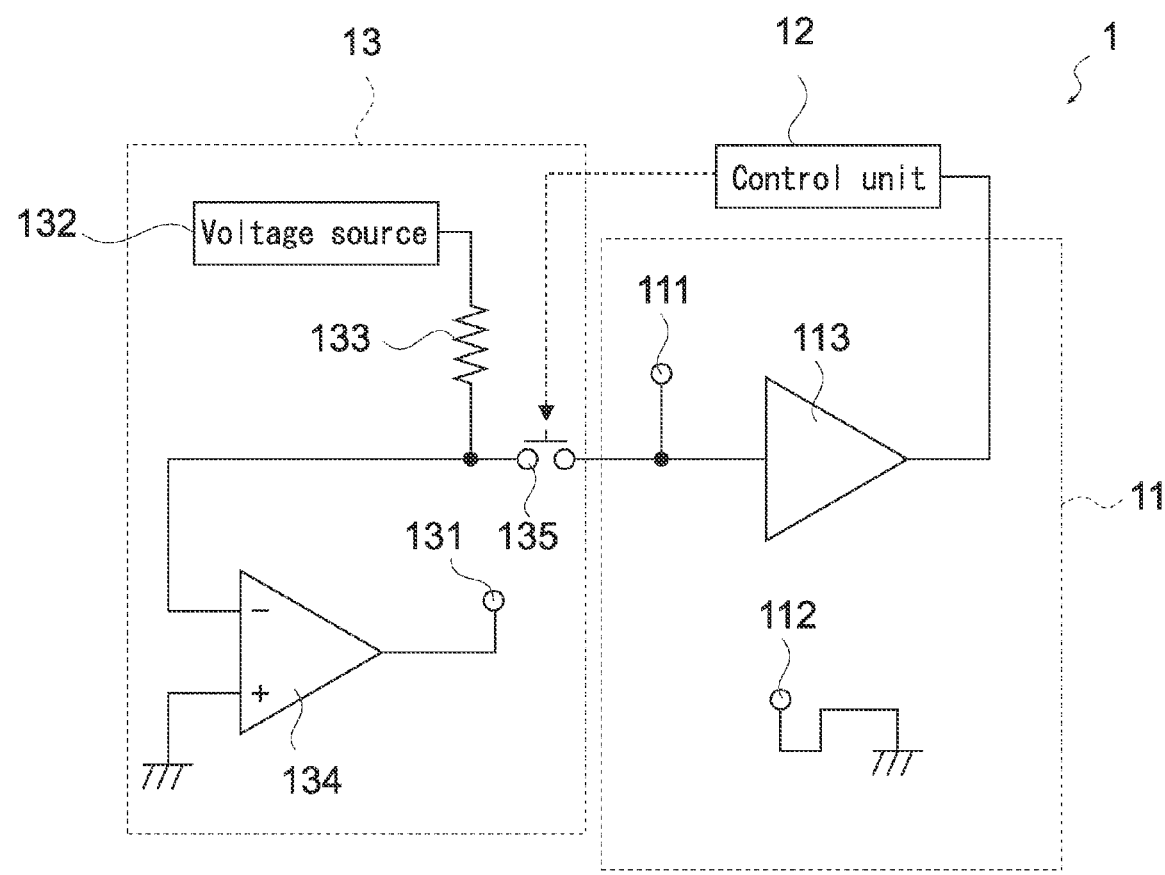
FIG. 5 is a schematic diagram showing a circuit configuration of the electroencephalogram activation apparatus according to the first embodiment.

Description is made of a circuit configuration of the electroencephalogram activation apparatus 1. FIG. 5 is a schematic diagram showing the circuit configuration of the electroencephalogram activation apparatus 1.

The electroencephalogram acquisition unit 11 includes a first electrode 111, a second electrode 112, and a first amplifier 113. The first electrode 111 is connected to an input terminal of the first amplifier 113, and an output terminal of the first amplifier 113 is connected to the control unit 12. The second electrode 112 is connected to a ground potential of the electroencephalogram activation apparatus 1 (hereinafter, simply referred to as ground potential).

The first electrode 111 is electrically connected to the scalp of the user. The first electrode 111 is an electrode which functions as a reference electrode for brain wave measurement, and can be held in contact with a position on the scalp of the user, at which brain waves can be effectively measured, such as the parietal region.

The second electrode 112 is electrically connected to the scalp of the user. The second electrode 112 is an electrode which functions as a comparison electrode at the time of brain wave measurement, and can be held in contact with a highly conductive position on the scalp of the user, such as the forehead.

The first amplifier 113 amplifies output of the first electrode 111 (potential difference with respect to the ground potential), which is input to the input terminal of the first amplifier 113, and then outputs the amplified output from the output terminal of the first amplifier 113. The first amplifier 113 may include amplifiers of any type such as a transistor.

The electroencephalogram acquisition unit 11 is configured as described above so as to amplify the potential difference between the first electrode 111 and the second electrode 112 with the first amplifier 113 and then output the amplified potential difference to the control unit 12. Note that, the number of the first electrode 111 and that of the second electrode 112 are not limited to one, and a plurality of first electrodes 111 and a plurality of second electrodes 112 may be arranged.

The electrical stimulation unit 13 includes a third electrode 131, a voltage source 132, a resistor 133, a second amplifier 134, and a change-over switch 135. The third electrode 131 is connected to an output terminal of the second amplifier 134. The voltage source 132 is connected to the resistor 133, and the resistor 133 is connected to an inverting input terminal (negative) of the second amplifier 134. A non-inverting input terminal (positive) of the second amplifier 134 is connected to the ground potential. The change-over switch 135 is connected to between the resistor 133 and the second amplifier 134, and also to between the first electrode 111 and the first amplifier 113 of the electroencephalogram acquisition unit 11.

The third electrode 131 is electrically connected to the scalp of the user. The third electrode 131 is an electrode which functions as a reference electrode for TES, and can be held in contact with a position on the scalp of the user, which is suitable to TES application.

The voltage source 132 is a voltage source configured to generate an activation voltage. The voltage source 132 may include an alternating-current voltage source or a direct-current voltage source.

Although description of the resistor 133 is made below in detail, when a resistance value of the resistor is sufficiently high, the electrical stimulation unit 13 can be prevented from having an influence on the electroencephalogram acquisition unit 11. The resistance value of the resistor 133 can be set, for example, to 100 MΩ or more.

The second amplifier 134 is an operational amplifier, and constitutes an inverting amplifier circuit when the change-over switch 135 is turned ON. Detailed description of the inverting amplifier circuit is made below.

The change-over switch 135 connects, in an on-off manner, a node between the resistor 133 and the second amplifier 134 and a node between the first electrode 111 and the first amplifier 113 in pairs to each other. When the change-over switch 135 is turned ON, the second amplifier 134 constitutes the inverting amplifier circuit as described above, and when the change-over switch 135 is turned OFF, the electrical stimulation unit 13 is disconnected from the electroencephalogram acquisition unit 11.

The electrical stimulation unit 13 is configured as described above so as to conduct an electric current between the third electrode 131 and the first electrode 111, that is, applies TES to the scalp of the user. Note that, the number of the third electrode 131 is not limited to one, and a plurality of third electrodes 131 may be arranged.

The control unit 12 is connected to the output terminal of the first amplifier 113 of the electroencephalogram acquisition unit 11 so as to control on/off of the change-over switch 135 in accordance with brain waves acquired by the electroencephalogram acquisition unit 11. The control unit 12 may include a microprocessor.

Figures 6, 7:
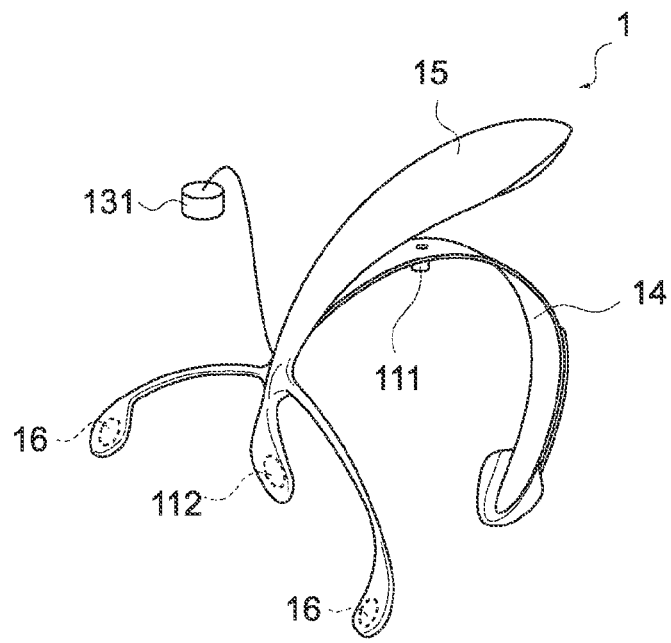
FIG. 6 is a list showing operation of the electroencephalogram activation apparatus according to the first embodiment and functions of electrodes.
FIG. 7 is a perspective view illustrating an external appearance of the electroencephalogram activation apparatus according to the first embodiment.

The electroencephalogram activation apparatus 1 can be configured to have the circuit configuration as described above. Next, description is made of operation of the electroencephalogram activation apparatus 1 having the above-mentioned circuit configuration. FIG. 6 is a list showing operation of the electroencephalogram activation apparatus 1 and functions of the electrodes.

First, when the change-over switch 135 is turned OFF, the first electrode 111 and the second electrode 112 function respectively as a reference electrode and a comparison electrode, and the potential difference between the first electrode 111 and the second electrode 112 is fed to the first amplifier 113. The first amplifier 113 amplifies and outputs the potential difference to the control unit 12. In other words, the electroencephalogram acquisition unit 11 acquires a brain wave. At this time, the change-over switch 135 is turned OFF. Thus, an electric current is not conducted to the electrical stimulation unit 13, and hence TES is not generated.

Next, when the change-over switch 135 is turned ON, the electroencephalogram acquisition unit 11 acquires a brain wave as described above. In the electrical stimulation unit 13, the voltage source 132, the resistor 133, the second amplifier 134, and the third electrode 131, and the first electrode 111 constitute the inverting amplifier circuit.

In the inverting amplifier circuit, the second amplifier 134 operates such that the potential difference between the non-inverting input terminal (positive) and the inverting input terminal (negative) becomes zero. With this, the first electrode 111 connected to the inverting input terminal is maintained at the ground potential. An electric current supplied by the voltage source 132 passes the resistor 133, and then flows from the first electrode 111 (comparison electrode having a ground potential) to the third electrode 131 (reference electrode having a negative potential). The first electrode 111 and the third electrode 131 are each connected to the scalp of the user, and hence the electric current is an electric current flowing through the brain of the user, that is, TES. This electric current is determined by a voltage generated by the voltage source 132 and the resistance value of the resistor 133, and maintains a fixed value irrespective of the resistance of the head of the user (resistance between the first electrode 111 and the third electrode 131).

As described above, the inverting amplifier circuit maintains the ground potential of the first electrode 111 and conducts a fixed electrical current from the first electrode 111 to the third electrode 131 irrespective of the resistance of the head of the user. Thus, according to this circuit configuration, without an influence on a brain wave to be measured (potential difference between the first electrode 111 and the second electrode 112), TES with preset intensity (electrical current between the first electrode 111 and the third electrode 131) can be applied.

Further, in the above-mentioned circuit configuration, the potential difference between the first electrode 111 (reference electrode) and the second electrode 112 (comparison electrode) under the state in which the change-over switch 135 is turned ON can be used for resistance measurement, the result of which indicates whether the electrodes are reliably connected to the scalp of the user.

The electroencephalogram activation apparatus 1 can be configured to have the circuit configuration as described above. In the above-mentioned circuit configuration, the control unit 12 is capable of turning ON/OFF the change-over switch 135, for example, with use of the analysis process and the sleep stage judgment as described above based on the brain wave obtained via the electroencephalogram acquisition unit 11, to thereby adjust the TES application timing. Further, the control unit 12 may be configured to control the voltage source 132 in addition to the change-over switch 135, to thereby adjust the intensity and the frequency of TES.

<Apparatus Structure of Electroencephalogram Activation Apparatus>

Description is made of an apparatus structure of the electroencephalogram activation apparatus 1. FIG. 7 is a perspective view illustrating an external appearance of the electroencephalogram activation apparatus 1. As illustrated in FIG. 7, the electroencephalogram activation apparatus 1 is a headgear attachable to the head of the user, and can be formed of a support portion 14 and a casing 15. Note that, the structure of the electroencephalogram activation apparatus 1 is not limited to that described herein.

The support portion 14 is a member configured to fix the electroencephalogram activation apparatus 1 to the head of the user, and is provided with the first electrode 111 and the second electrode 112 described above. The first electrode 111 and the second electrode 112 are provided at respective predetermined positions. For example, the first electrode 111 is provided at the position held in contact with the parietal region of the user, and the second electrode 112 is provided at the position held in contact with the forehead of the user. Further, the third electrode 131 is connected to the support portion 14 with a cord such that the user can arrange the third electrode 131 at any position on the scalp of him/herself.

The casing 15 accommodates various electronic components of the electroencephalogram activation apparatus 1, that is, the first amplifier 113, the control unit 12, the second amplifier 134, and the voltage source 132. As shown in FIG. 5, those electronic components are connected to the electrodes with wires (not shown) provided to the support portion 14. The casing 15 may accommodate a storage device configured to store brain wave measurement results, TES application records, and the like, a wireless communication device configured to communicate with external apparatuses, and the like. Note that, the control unit 12 may be attached to the external apparatus. In this case, the control unit 12 is capable of being connected to the electroencephalogram acquisition unit 11 and the electrical stimulation unit 13 with the wireless communication device.

Further, the electroencephalogram activation apparatus 1 may include eye movement electrodes 16. The eye movement electrodes 16 are electrodes configured to acquire eye movement (EOG) to be referred to together with an electroencephalogram at the time when the control unit 12 judges the sleep stage, and can be arranged on the left and right temples of the user. The eye movement electrodes 16 are connected to the control unit 12 with wires (not shown), and feed measurement results of eye movement to the control unit 12.

As described above, the electroencephalogram activation apparatus 1 according to this embodiment can be mounted to one headgear. By wearing the headgear, the user can use the electroencephalogram activation apparatus 1.

<Effects of Electroencephalogram Activation Apparatus According to this Embodiment>

In the electroencephalogram activation apparatus 1 according to this embodiment, the control unit 12 controls the electrical stimulation unit 13 based on the brain wave acquired by the electroencephalogram acquisition unit 11, and hence effective TES can be applied in accordance with brain activity of the user.

In particular, in the electroencephalogram activation apparatus 1, the control unit 12 refers to the potential density in the frequency range of the brain wave activated by TES, and hence an effect of TES can be directly grasped. As a result, more effective TES can be applied.

Further, in the electroencephalogram activation apparatus 1, the control unit 12 judges the sleep stage based on brain waves, and controls the electrical stimulation unit 13 in accordance with this sleep stage. With this, TES can be applied at an effective timing.

The electroencephalogram activation apparatus 1 configured as described above can be obtained with the above-mentioned circuit configuration. According to this circuit configuration, TES with preset intensity can be applied without an influence on a brain wave to be measured.

As described above, the electroencephalogram activation apparatus 1 according to this embodiment is capable of applying TES in accordance with a condition of brain activity of the user.

(Second Embodiment)

Description is made of an electroencephalogram activation apparatus according to a second embodiment. In this embodiment, description of the same components as those in the first embodiment is omitted. The electroencephalogram activation apparatus according to this embodiment is different from the electroencephalogram activation apparatus 1 according to the first embodiment in circuit configuration and apparatus structure.

<Circuit Configuration of Electroencephalogram Activation Apparatus>

Figure 8:
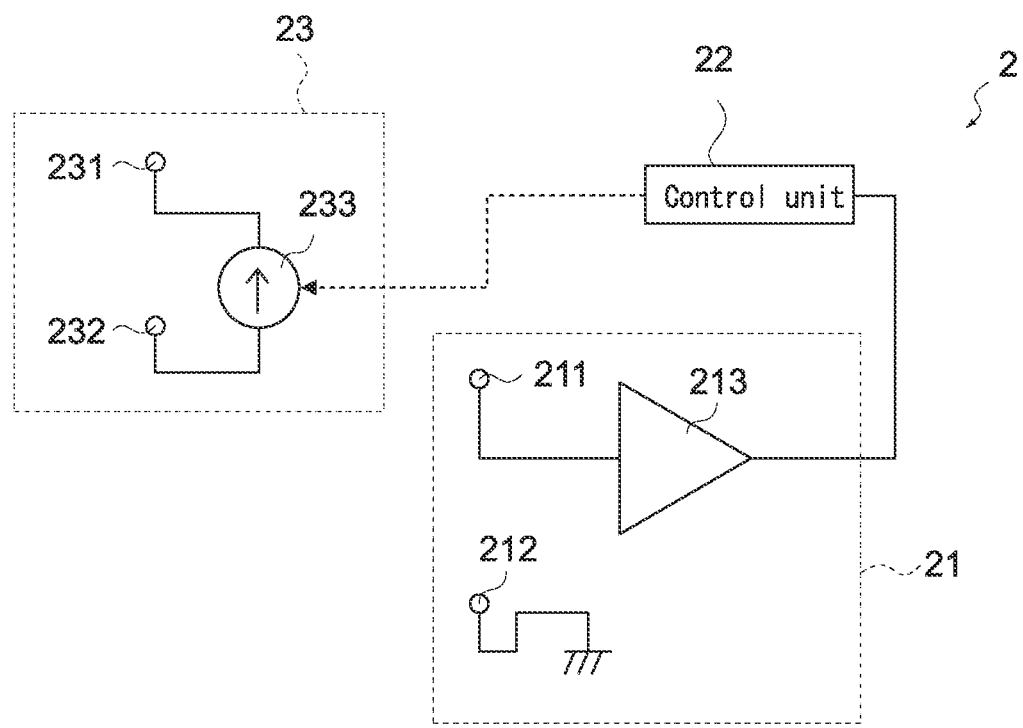
FIG. 8 is a schematic diagram showing a circuit configuration of an electroencephalogram activation apparatus according to a second embodiment.

FIG. 8 is a schematic diagram showing a circuit configuration of the electroencephalogram activation apparatus 2 according to the second embodiment. As shown in FIG. 8, the electroencephalogram activation apparatus 2 is formed of an electroencephalogram acquisition unit 21, a control unit 22, and an electrical stimulation unit 23. Functional configurations of the electroencephalogram acquisition unit 21, the control unit 22, and the electrical stimulation unit 23 are the same as those described in the first embodiment.

The electroencephalogram acquisition unit 21 includes a first electrode 211, a second electrode 212, and an amplifier 213. The first electrode 211 is connected to an input terminal of the amplifier 213, and an output terminal of the amplifier 213 is connected to the control unit 22. The second electrode 212 is connected to a ground potential of the electroencephalogram activation apparatus 2.

The first electrode 211 is electrically connected to the scalp of the user. The first electrode 211 is an electrode which functions as a reference electrode at the time of brain wave measurement, and can be held in contact with a position on the scalp of the user, at which brain waves can be effectively measured, such as the parietal region.

The second electrode 212 is electrically connected to the scalp of the user. The second electrode 212 is an electrode which functions as a comparison electrode at the time of brain wave measurement, and can be held in contact with a highly conductive position on the scalp of the user, such as the forehead.

The amplifier 213 amplifies output of the first electrode 211 (potential difference with respect to the ground potential), which is input to the input terminal of the amplifier 213, and then outputs the amplified output from the output terminal of the amplifier 213. The amplifier 213 may include amplifiers of any type such as a transistor.

The electroencephalogram acquisition unit 21 is configured as described above so as to amplify the potential difference between the first electrode 211 and the second electrode 212 with the amplifier 213 and then output the amplified potential difference to the control unit 22. Note that, the number of the first electrode 211 and that of the second electrode 212 are not limited to one, and a plurality of first electrodes 211 and a plurality of second electrodes 212 may be arranged.

The electrical stimulation unit 23 includes a third electrode 231, a fourth electrode 232, and an electric current source 233. The third electrode 231 and the fourth electrode 232 are connected to the electric current source 233.

The third electrode 231 is electrically connected to the scalp of the user. The third electrode 231 is an electrode configured to conduct an electric current to be conducted as TES between the third electrode 231 and the fourth electrode 232, and can be held in contact with a position on the scalp of the user, which is suitable to application of TES.

The fourth electrode 232 is electrically connected to the scalp of the user. The fourth electrode 232 is an electrode configured to conduct the electric current to be conducted as TES between the fourth electrode 232 and the third electrode 231, and can be held in contact with a position on the scalp of the user, which is suitable to application of TES.

The electric current source 233 applies the electric current to be conducted as TES between the third electrode 231 and the fourth electrode 232. The electric current source 233 may include an alternating-current voltage source or a direct-current voltage source.

The electrical stimulation unit 23 is configured as described above so as to conduct an electric current between the third electrode 231 and the fourth electrode 232, that is, applies TES to the scalp of the user. The number of the third electrode 231 and that of the fourth electrode 232 are not limited to one, and a plurality of third electrodes 231 and a plurality of fourth electrodes 232 may be arranged.

The control unit 22 is connected to the output terminal of the amplifier 213 of the electroencephalogram acquisition unit 21 so as to control the electric current source 233 in accordance with brain waves acquired by the electroencephalogram acquisition unit 21.

In the circuit configuration as described above, when the electroencephalogram acquisition unit 21 acquires a brain wave and the electrical stimulation unit 23 applies TES simultaneously therewith, there is a risk that the electroencephalogram acquisition unit 21 detects not only the brain waves but also TES itself. However, the control unit 22 is capable of referring to the potential density of the brain wave in the frequency range of being activated by TES (not including the frequency of TES), and this potential density does not include potential density of TES itself. Thus, the control unit 22 is capable of controlling the electrical stimulation unit 23 based on the brain wave free from an influence of TES itself.

<Apparatus Structure of Electroencephalogram Activation Apparatus>

Figure 9:
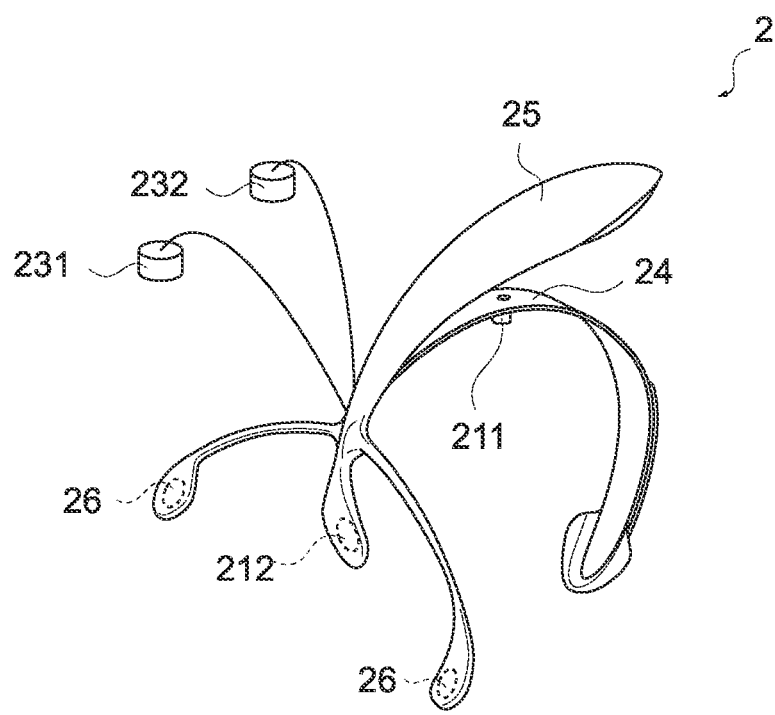
FIG. 9 is a perspective view illustrating an external appearance of the electroencephalogram activation apparatus according to the second embodiment.

Description is made of an apparatus structure of the electroencephalogram activation apparatus 2. FIG. 9 is a perspective view illustrating an external appearance of the electroencephalogram activation apparatus 2. As illustrated in FIG. 9, the electroencephalogram activation apparatus 2 is a headgear attachable to the head of the user, and can be formed of a support portion 24 and a casing 25. Note that, the structure of the electroencephalogram activation apparatus 2 is not limited to that described herein.

The support portion 24 is a member configured to fix the electroencephalogram activation apparatus 2 to the head of the user, and is provided with the first electrode 211 and the second electrode 212 described above. The first electrode 211 and the second electrode 212 are provided at respective predetermined positions. For example, the first electrode 211 is provided at the position held in contact with the parietal region of the user, and the second electrode 212 is provided at the position held in contact with the forehead of the user. Further, the third electrode 231 and the fourth electrode 232 are connected to the support portion 24 with cords such that the user can arrange the third electrode 231 and the fourth electrode 232 at any position on the scalp of him/herself.

The casing 25 accommodates various electronic components of the electroencephalogram activation apparatus 2, that is, the amplifier 213, the electric current source 233, and the control unit 22. As shown in FIG. 8, those electronic components are connected to the electrodes with wires (not shown) provided to the support portion 24. The casing 25 may accommodate a storage device configured to store brain wave measurement results, TES application records, and the like, a wireless communication device configured to communicate with external apparatuses, and the like. Note that, the control unit 22 may be attached to the external apparatus. In this case, the control unit 22 can be connected to the electroencephalogram acquisition unit 21 and the electrical stimulation unit 23 with the wireless communication device.

Further, the electroencephalogram activation apparatus 2 may include eye movement electrodes 26. The eye movement electrodes 26 are electrodes configured to acquire eye movement (EOG) to be referred to together with an electroencephalogram at the time when the control unit 22 judges the sleep stage, and can be arranged on the left and right temples of the user. The eye movement electrodes 26 are connected to the control unit 22 with wires (not shown), and feed measurement results of eye movement to the control unit 22.

As described above, the electroencephalogram activation apparatus 2 according to this embodiment can be mounted to one headgear. By wearing the headgear, the user can use the electroencephalogram activation apparatus 2.

<Effects of Electroencephalogram Activation Apparatus According to this Embodiment>

In the electroencephalogram activation apparatus 2 according to this embodiment, the control unit 22 controls the electrical stimulation unit 23 based on the brain wave acquired by the electroencephalogram acquisition unit 21, and hence effective TES can be applied in accordance with brain activity of the user.

In particular, in the electroencephalogram activation apparatus 2, the control unit 22 refers to the potential density in the frequency range of the brain wave activated by TES, and hence an effect of TES can be directly grasped. As a result, more effective TES can be applied. Further, even when the electroencephalogram acquisition unit 21 detects not only brain waves but also TES itself, the electroencephalogram activation apparatus 2 is capable of controlling the electrical stimulation unit 23 based on the brain wave free from the influence of TES itself.

As described above, the electroencephalogram activation apparatus 2 according to this embodiment is capable of applying TES in accordance with a condition of brain activity of the user.

The present technology is not limited to those embodiments, and can be changed without departing from the gist of the present technology.

Note that, the present technology may employ the following configurations.

(1) An electroencephalogram activation apparatus, including:

an electroencephalogram acquisition unit configured to acquire brain waves of a user;

an electrical stimulation unit configured to apply transcranial electrical stimulation to the scalp of the user; and a control unit configured to control the electrical stimulation unit based on the brain waves acquired by the electroencephalogram acquisition unit.

(2) The electroencephalogram activation apparatus according to Item (1), in which the electrical stimulation unit applies transcranial electrical stimulation at a certain frequency to the scalp of the user, and the control unit controls the electrical stimulation unit in accordance with potential density in a frequency range of a brain wave activated by the transcranial electrical stimulation at the certain frequency.

(3) The electroencephalogram activation apparatus according to Item (1) or (2), in which the control unit judges one of a plurality of sleep stages of the user based on a characteristic waveform which appears in the brain waves, and controls the electrical stimulation unit in accordance with the sleep stage.

(4) The electroencephalogram activation apparatus according to any one of Items (1) to (3), in which the electroencephalogram acquisition unit includes a first electrode to be held in contact with the scalp of the user, a first amplifier having an input terminal to which the first electrode is connected, and a second electrode connected to a ground potential and to be held in contact with the head of the user, the electrical stimulation unit includes a voltage source, a resistor connected to the voltage source, a second amplifier having an inverting input terminal to which the resistor is connected, and a non-inverting input terminal to which the ground potential is connected, and a third electrode connected to an output terminal of the second amplifier and to be held in contact with the head of the user, and the control unit is connected to an output terminal of the first amplifier and controls the electrical stimulation unit based on a brain wave which is a potential difference between output of the first amplifier and the ground potential.

(5) The electroencephalogram activation apparatus according to any one of Items (1) to (4), in which the electroencephalogram acquisition unit includes a first electrode to be held in contact with the scalp of the user, an amplifier having an input terminal to which the first electrode is connected, and a second electrode connected to a ground potential and to be held in contact with the head of the user, the electrical stimulation unit includes an electric current source, a third electrode connected to the electric current source and to be held in contact with the scalp of the user, and a fourth electrode connected to the electric current source and to be held in contact with the scalp of the user, and the control unit is connected to an output terminal of the amplifier and controls the electrical stimulation unit based on a brain wave which is a potential difference between output of the amplifier and the ground potential.

(6) The electroencephalogram activation apparatus according to any one of Items (1) to (5), in which the electrical stimulation unit applies slow oscillation as the transcranial electrical stimulation, and the control unit controls the electrical stimulation unit based on potential density of a brain wave within a frequency range of a θ wave.

(7) The electroencephalogram activation apparatus according to any one of Items (1) to (6), in which the control unit applies the transcranial electrical stimulation to the electrical stimulation unit when the sleep stage is Stage 2, and is free from applying the transcranial electrical stimulation to the electrical stimulation unit when the sleep stage is other than Stage 2.

The present disclosure contains subject matter related to that disclosed in Japanese Priority Patent Application JP 2011-113452 filed in the Japan Patent Office on May 20, 2011, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An electroencephalogram activation apparatus, comprising:

an electroencephalogram acquisition unit configured to acquire brain waves of a user;

an electrical stimulation unit configured to apply transcranial electrical stimulation to a scalp of the user; and a control unit configured to control the electrical stimulation unit based on the brain waves acquired by the electroencephalogram acquisition unit, wherein, the electrical stimulation unit applies transcranial electrical stimulation at a given frequency to the scalp of the user, and the control unit controls the electrical stimulation unit in accordance with potential density in a frequency range of a brain wave activated by the transcranial electrical stimulation at the given frequency.

2. The electroencephalogram activation apparatus according to claim 1, wherein the control unit judges one of a plurality of sleep stages of the user based on a characteristic waveform that appears in the brain waves, and controls the electrical stimulation unit in accordance with the sleep stage.

3. The electroencephalogram activation apparatus according to claim 2, wherein the control unit applies the transcranial electrical stimulation to the electrical stimulation unit when the sleep stage is Stage 2, and does not apply the transcranial electrical stimulation to the electrical stimulation unit when the sleep stage is other than Stage 2.

4. The electroencephalogram activation apparatus according to claim 1, wherein:
   (1) the electroencephalogram acquisition unit includes
      (a) a first electrode to be held in contact with the scalp of the user,
      (b) a first amplifier having an input terminal to which the first electrode is connected, and
      (c) a second electrode connected to a ground potential and to be held in contact with a head of the user,
   (2) the electrical stimulation unit includes
      (a) a voltage source,
      (b) a resistor connected to the voltage source,
      (c) a second amplifier having an inverting input terminal to which the resistor is connected and a non-inverting input terminal to which the ground potential is connected, and
      (d) a third electrode connected to an output terminal of the second amplifier and to be held in contact with the head of the user, and
   (3) the control unit is connected to an output terminal of the first amplifier and controls the electrical stimulation unit based on a brain wave corresponding to a potential difference between an output of the first amplifier and the ground potential.

5. The electroencephalogram activation apparatus according to claim 1, wherein:
   (1) the electroencephalogram acquisition unit includes
      (a) a first electrode to be held in contact with the scalp of the user,
      (b) an amplifier having an input terminal to which the first electrode is connected, and
      (c) a second electrode connected to a ground potential and to be held in contact with a head of the user,
   (2) the electrical stimulation unit includes
      (a) an electric current source,
      (b) a third electrode connected to the electric current source and to be held in contact with the scalp of the user, and
      (c) a fourth electrode connected to the electric current source and to be held in contact with the scalp of the user, and
   (3) the control unit is connected to an output terminal of the amplifier and controls the electrical stimulation unit based on a brain wave corresponding to a potential difference between an output of the amplifier and the ground potential.

6. The electroencephalogram activation apparatus according to claim 1, wherein:
   the electrical stimulation unit applies slow oscillation as the transcranial electrical stimulation, and
   the control unit controls the electrical stimulation unit based on potential density of a brain wave within a frequency range of a $\theta$ wave.

7. The electroencephalogram activation apparatus according to claim 1, wherein the electroencephalogram activation apparatus is configured as a headgear that can be worn by the user.

8. The electroencephalogram activation apparatus according to claim 7, wherein the electroencephalogram activation apparatus further comprises a support unit configured to fix the electroencephalogram activation apparatus to a head of the user.

9. The electroencephalogram activation apparatus according to claim 1, wherein the electroencephalogram activation apparatus further comprises a wireless communication device configured to communicate with an external apparatus.

10. The electroencephalogram activation apparatus according to claim 1, wherein the electroencephalogram activation apparatus further comprises a storage device.

* * * * *